United States Patent [19]

Wright

[11] Patent Number: 5,795,582
[45] Date of Patent: Aug. 18, 1998

[54] ADJUVANT PROPERTIES OF POLY (AMIDOAMINE) DENDRIMERS

[75] Inventor: D. Craig Wright, Gaithersburg, Md.

[73] Assignee: Novavax, Inc., Columbia, Md.

[21] Appl. No.: 597,938

[22] Filed: Feb. 7, 1996

[51] Int. Cl.$^6$ .............. A61K 9/00; A61K 47/48
[52] U.S. Cl. .............. 424/400; 424/78.17; 424/DIG. 16
[58] Field of Search .............. 424/400, 78.17, 424/DIG. 16

[56] References Cited

U.S. PATENT DOCUMENTS

| | | | |
|---|---|---|---|
| 4,587,329 | 5/1986 | Tomalia et al. | 528/363 |
| 5,338,532 | 8/1994 | Tomalia et al. | 424/1.49 |
| 5,482,698 | 1/1996 | Griffiths | 424/141 |

OTHER PUBLICATIONS

International Search Report, PCT/US97/01664 dated Apr. 7, 1996.

*Primary Examiner*—Joseph L. Schofer
*Assistant Examiner*—Wu C. Cheng
*Attorney, Agent, or Firm*—Lahive & Cockfield, LLP

[57] ABSTRACT

A new method of adjuvanting a variety of materials has been developed. Starburst dendrimers, primarily poly (amidoamine) starburst dendrimers, can be used as an adjuvant for Influenza antigen and similar materials. Mid-Generation dendrimers are preferred and yield high antibody titer levels with reduced antigen dosage.

16 Claims, 2 Drawing Sheets

ADJUVANT PROPERTIES OF POLY (AMIDOAMINE) DENDRIMERS

The present invention concerns the use of poly (amidoamine) dendrimers as adjuvants for enhancing the immune response to a variety of antigens. These poly (amidoamine) dendrimers are particularly useful in vaccines because lower doses of the antigen can be used than in unadjuvanted vaccines.

Dendrimers, as the term is used herein, are a class of polymers often called starburst polymers because of their shape. These dendrimers have a molecular architecture with an initiator core, interior layers (or "generations") of repeating units regularly attached to this initiator core, and an exterior surface of terminal groups attached to the outermost generation. These starburst polymers are radially symmetrical and have a branched or tree-like structure. The number of generations can be controlled by the conditions of manufacture, leading to different size molecules having different numbers of terminal groups. U.S. Pat. No. 4,587, 329 entitled *Dense Star Polymers Having Two Dimensional Molecular Diameter*, issued May 6, 1986 to the Dow Chemical Company, the disclosure of which is incorporated by reference, describes these starburst dendrimers and methods of their manufacture. These starburst dendrimers can be made to exact, repeatable molecular weights with the same number of functional groups on each dendrimer. These functional groups can react with a material to be carried, such as a pharmaceutical or agricultural product, or the material to be carried can be associated with this dendrimer in a non-reactive manner.

Figure 1:
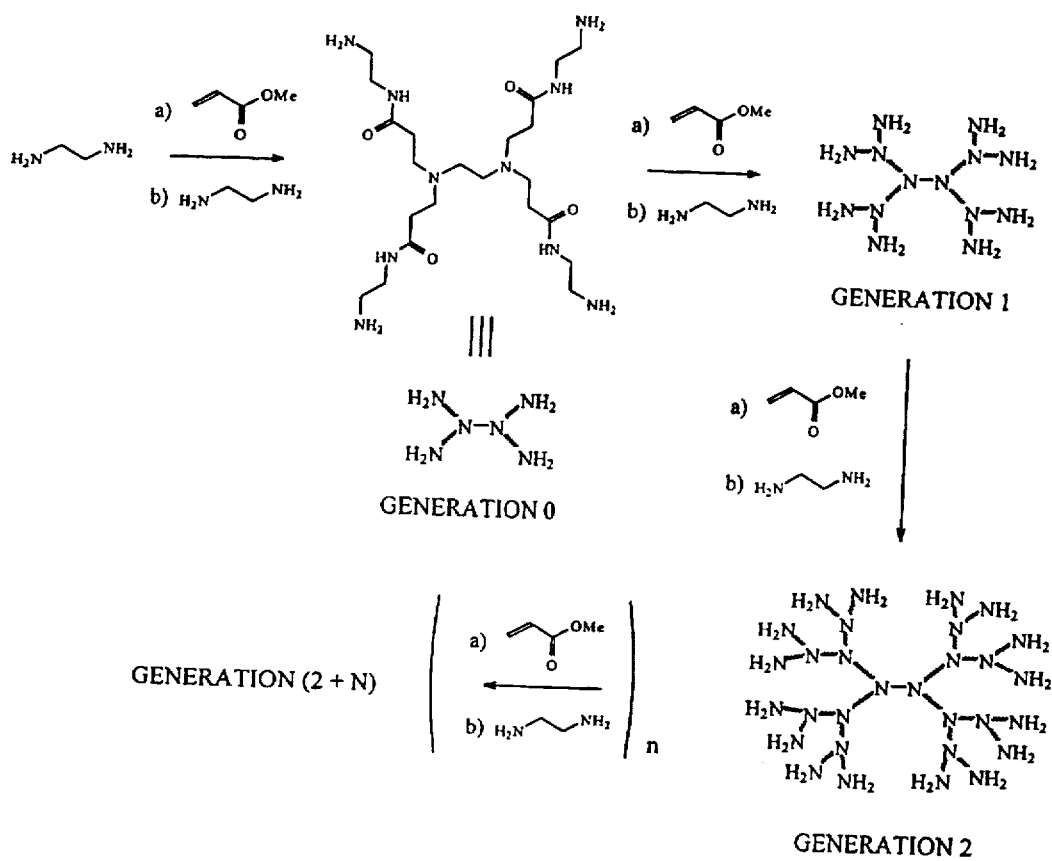

The family of dendrimers useful in the present invention are based on an amidoamine repeat structure, forming what are known as poly(amidoamine) dendrimers ("PAMAM"). PAMAM dendrimers are grown from an amine containing core structure such as ammonia, ethylene diamine, or the like. Normally ethylene diamine is used as the core or initiator of the reaction. FIG. 1 shows the basic synthesis for the first three generations of these PAMAM starburst dendrimers. Ethylene diamine (EDA) is reacted with methyl acrylate under control conditions such that a Michael addition of one molecule of EDA to four molecules of methyl acrylate occurs. This forms the initiator or core adduct. Following the removal of excess methyl acrylate, the core adduct is reacted with an excess of EDA to form a 0 generation molecule having four amidoamine groups. The excess EDA is removed and the 0 generation molecule can be reacted with methyl acrylate in another Michael addition reaction to form a first generation molecule containing eight primary amine groups. A continuation of this stepwise procedure forms the other generations in sequence. Table 1 list the molecular weight and number of primary amine groups for the generation 0-10 PAMAM starburst dendrimers.

TABLE 1

| Generation | MW | Primary Amino Groups |
|---|---|---|
| 0 | 517 | 4 |
| 1 | 1430 | 8 |
| 2 | 3256 | 16 |
| 3 | 6909 | 32 |
| 4 | 14215 | 64 |
| 5 | 28826 | 128 |
| 6 | 58048 | 256 |
| 7 | 116493 | 512 |
| 8 | 233383 | 1024 |

TABLE 1-continued

| Generation | MW | Primary Amino Groups |
|---|---|---|
| 9 | 467126 | 2048 |
| 10 | 934787 | 4096 |

As noted, these starburst polymers have been known to be useful with a variety of pharmaceuticals and agricultural products. In addition, it has been theorized that they may have immuno-potentiating response. See U.S. Pat. No. 5,338,532, entitled: *Starburst Adjuvants*, issued Aug. 16,1994, to the Dow Chemical Company, the disclosure of which is also incorporated herein by reference. However, there are no tests shown of this proposed immunopotentiating effect.

Vaccines are composed of antigens which, when administered systematically, predominately stimulate an antibody response. Adjuvants are materials which enhance the ability of the antigen or vaccine to generate an antibody response or cytotoxic T cell response in vivo. Adjuvants are necessary for a number of antigens since the immune response maybe too low without the adjuvant to provide a protective level of antibody. Adjuvants enhance the immune response of the body, yielding higher titers and requiring lesser dosages of antigen. However, the only approved adjuvant for human use in the United States is aluminum hydroxide, also known as alum. Adjuvanted vaccines are presently prepared by absorbing antigens on alum and then injecting these materials intramuscularly. Examples of alum adjuvanted vaccines include Diphtheria and Tetanus toxoid vaccines.

A problem with the use of alum in a number of vaccines is that certain alum-antigen complexes can be toxic. This is the exact problem with using an alum adjuvant for an Influenza vaccine. Present Influenza vaccines are nonadjuvanted, since Influenza absorbed onto alum is toxic. For this reason, although Influenza vaccine has been approved for human use since the 1950s, it has never been approved in any type of adjuvanted form.

Accordingly, an object of the invention is to provide an adjuvanted vaccine which is physiologically safe and effective.

Another object of the invention is to provide an Influenza vaccine using a starburst dendrimer as an adjuvant.

A further object of the invention is to provide a method of immunizing humans against Influenza using a starburst dendrimer-adjuvanted vaccine.

These and other objects and features of the invention will be apparent in the following description and the drawings.

SUMMARY OF THE INVENTION

The present invention features a vaccine having a starburst dendrimer as an adjuvant. The preferred vaccine is for Influenza and contains an effective amount of a composition formed of an Influenza antigen and a starburst dendrimer in a physiologically compatible carrier. The use of the starburst dendrimer makes it possible to adjuvant Influenza without producing a toxic complex since even a small amount of the dendrimer acts as an effective adjuvant. The use of a dendrimer as an adjuvant makes it possible to use an amount of Influenza antigen which is substantially reduced from the amount necessary to yield a compatible antigenic response if the antigen is given without the dendrimer. The preferred dendrimer is a poly(amidoamine) dendrimer, preferably a Generation 3-Generation 10 dendrimer, more preferably a Generation 3-Generation 8 dendrimer, with Generation 6 being the most preferred dendrimer. Although any Influenza virus antigen could be used in the composition, a composition containing multiple Influenza virus antigens such as trivalent split virus Influenza antigens, are preferred. The physiologically compatible carrier is preferrably selected from the group consisting of distilled water, phosphate buffered saline, normal saline, and mixtures thereof; however, any other physiologically compatible carrier could be used. The starburst dendrimers can be used in a dilute form, thereby avoiding any potential problems that may stem from use in more concentrated form, such as toxic side effects.

The invention further features a method of preparing a vaccine for protection against illnesses, primarily viral illnesses such as Influenza. The vaccine used in this method uses a lower level of antigen than conventional vaccines due to the adjuvant properties of the starburst dendrimers. Briefly, the Influenza antigen, which may be a single antigen or a multiple antigen such as a trivalent split virus antigen, is mixed with the starburst dendrimer and the resulting mixture is diluted with a physiologically compatible carrier. The same type of dendrimers as described previously are preferably used in this method.

One advantage of the PAMAM dendrimers is their positive charge. These PAMAM dendrimers adhere or bind more easily to proteins or other compounds with negative isoelectric focusing points. Influenza virus, when in antigenic form, has such a negative isoelectric focusing point. Other viruses, or antigenic determinants of viruses, bacteria, fungi, or parasites which have such a negative isoelectric focusing point, can also be used in the methods of the invention.

Other features of the invention will be readily apparent from the detailed description.

BRIEF DESCRIPTION OF THE DRAWING

FIG. 1 of the drawing shows the formation of Generation 0, Generation 1 and Generation 2 PAMAM dendrimers by Michael addition of ethylene diamine and methyl acrylate; and FIG. 2 of the drawing shows the correlation between the number of primary amine groups in three generations of dendrimers plotted against the mean IFA titer from mice immunized with vaccine adjuvanted with those dendrimers.

DETAILED DESCRIPTION OF THE INVENTION

The present invention utilizes the adjuvant properties of dendrimers, primarily mid-Generation poly(amidoamine) dendrimers, to provide an antigenic response which is much greater than is otherwise available. The use of these dendrimers allows very low levels of antigen to be used, making this an economically viable and safe method. In addition, the dendrimers are used at a very low level as well, providing protection against dendrimer toxicity.

For test purposes, an Influenza vaccine was used. This was commercially available trivalent split virus Influenza vaccine, a subvirion flu vaccine, obtained from Pasteur Merieux. The vaccine is made by inoculating embryonated eggs with virus and aspirating the infected fluid 3 days later. The Influenza virus is then purified by ultracentrifugation, disrupted with detergent to split the virus, and undergoes several additional purification steps before being resuspended in phosphate buffered saline. While it is not completely clear precisely what antigens are involved in the immune response, it is assumed that the hemaglutinating antigen on the surface of the virus is one of the protective antigens.

The following examples show the efficacy of the present invention.

EXAMPLE I

In this example, a commercially prepared trivalent split virus Influenza vaccine was used to show antigenic response and safety. Generation 6 PAMAM dendrimers having 256 amidoamine groups (MW 58,048) obtained from Dendritech, Inc. of Midland, Mich., were brought to pH 7.4 by the addition of concentrated hydrochloric acid. Dendrimers are presently available suspended in methanol. Before they can be used in the practice of this invention, the methanol should be removed, e.g., rotoevaporate to dryness, after which the pH should be titrated to neutral with concentrated HCl. The dendrimers may then be resuspended in a pharmaceutically compatible solution, such as $H_2O$ or PBS. Other methods of removing the methanol carrier will occur to those skilled in the art, and are encompassed by the methods of the invention. This dendrimer solution was mixed with the trivalent Influenza vaccine at a concentration of 35 μg/mL, yielding final concentrations of 29 mg/mL PAMAM dendrimer and 21 μg/mL Influenza vaccine. Two 10-fold serial dilutions of the vaccine/dendrimer product were performed and compared with similar serial dilutions of the dendrimer alone and the Influenza antigen alone.

Groups of 6 week old C3H female mice (7–10 mice per group) were injected with the dendrimer alone, Influenza antigen alone, or the PAMAM dendrimer adjuvanted-Influenza vaccine. The animals were prebled at day 0, and then bled on day 31 after initial immunization. The animals were re-immunized on day 34 after initial immunization and then sacrificed and bled out on day 65. Indirect immunofluorescent assays (IFA) were conducted on all bleeding samples and hemagglutination inhibition assays (HI) were performed only on the terminal bleeding sample because of the large amount of blood needed. The results of all assays are reported as the reciprocal of the highest titer of antisera detected as positive. Table 2 shows the results of the IFA testing and the HI testing.

As can be seen from Table 3, the undiluted Influenza/dendrimer vaccine was too concentrated; in fact, it was toxic and all of the animals died within two hours of the first injection. The dendrimer itself, at the same 2.9 mg/mL concentration, also caused death in the same time period. Accordingly, only diluted form (1:10 and 1:100) data is shown in Table 2. As can be seen from Tables 2 and 3, dilute concentrations of dendrimers have a significant adjuvant effect, with no toxicity.

TABLE 2

Immunogenicity of G6 Dendrimer-Influenza Vaccine in *Mus musculus* strain C3H

| Murine Strain | IFA Antigen: A/Texas H1N1 | Amount HA in Micrograms | Amount of Dendrimers in Milligrams | Pre-bleed Reciprocal IFA | Day 34 Reciprocal Mean IFA | Final Day Reciprocal Mean IFA | Final Day Mean HI |
|---|---|---|---|---|---|---|---|
| C3H 10/group | Pasteur Merieux Subvirion Flu PBS mixed - IM (Influenza Ag alone) | 1.7 | 0 | 0 | NP | 240 (day 42) | 56 (day 42) |
| C3H 10/group | PM Subvirion Flu PBS mixed w/Dendrimers, pH = 7.4, diluted 1:10 (Influenza and G6 Dendrimers) | 0.21 | 0.29 | 0 | 2586 | 4096 (day 42) | 1680 (day 42) |
| C3H 8/group | PM Subvirion Flu Diluted 1:10 with PBS (Influenza Ag alone) | 0.17 | 0 | 0 | 36 | 176 (day 65) | 41 (day 65) |
| C3H 10/group | PM Subvirion Flu PBS mixed w/Dendrimers pH = 7.4, diluted 1:100 (Influenza and G6 Dendrimers) | 0.021 | 0.02 | 0 | 109 | 448 (day 65) | 256 (day 65) |
| C3H 7/group | PM Subvirion Flu Diluted 1:100 with PBS (Influenza Ag alone) | 0.017 | 0 | 0 | 0.6 (2/7 resp.) | 20 (6/7 resp.) (day 65) | NP (day 65) |

Volume of Vaccine Innoculum per mouse 100 μL-IM
NP = not performed

TABLE 3

Toxicity of G6 Dendrimer-Influenza Vaccine in *Mus musculus* strain C3H

| Murine Strain | IFA Antigen: A/Texas H1N1 |
|---|---|
| C3H 10/group | Dendrimers = 7.4 (G6) undiluted (29 mg/mL) (All animals died within 2 hours of injection) |
| C3H 10/group | PM Subvirion Flu PBS mixed w/Dendrimers pH = 7.4 (G6) undiluted (All ten animals died within 2 hours of injection) |
| C3H 10/group | Pasteur Merieux Subvirion Flu PBS mixed - IM (All ten animals alive at day 42 after 2 injections) |
| C3H 10/group | PM Subvirion Flu PBS mixed w/Dendrimers pH = 7.4 (G-6) diluted 1:10 (All ten animals alive 65 days after 2 injections) |
| C3H 8/group | PM Subvirion Flu Diluted 1:10 with PBS (All eight animals alive 65 days after 2 injections) |
| C3H 10/group | PM Subvirion Flu PBS mixed w/Dendrimers pH = 7.4, diluted 1:100 (All ten animals alive 65 days after 2 injections) |
| C3H 7/group | PM Subvirion Flu Diluted 1:100 with PBS (All seven animals alive 65 days after 2 injections) |

Volume of Vaccine Innoculum per mouse 100 μL-IM

Comparison of the 1:10 antigen/dendrimer vaccine with the same amount of vaccine alone shows the effectiveness of the invention. After only one injection, the non-adjuvanted vaccine had a titer of 36 while the adjuvanted had a titer greater than 2500, a 71-fold increase. Similarly after the second injection, the values are 176 and 4,096, respectively, an improvement of over 23 fold. The results at the higher dilution, the 1:100 dilution, are just as dramatic. After a single injection, there is a 181-fold greater response from the adjuvanted vaccine and after the second injection, there is better than 22-fold increase in response. In fact, the value after two injections with 100 fold dilution of the antigen/dendrimer vaccine antigenic response than the 1:10 dilution of the antigen alone.

The hemagglutionation inhibition assay (HI) yield similar results. Undiluted Influenza antigen yielded a titer of 56 while the antigen/dendrimer combination yielded titers of 1680 and 256 at 1:10 and 1:100 dilutions, respectively. A titer of 32 is normally considered necessary for effectiveness.

In light of the foregoing, it is clear that the dendrimers act as exceptional adjuvants, even on materials that are notoriously difficult to adjuvant.

Figure 2:
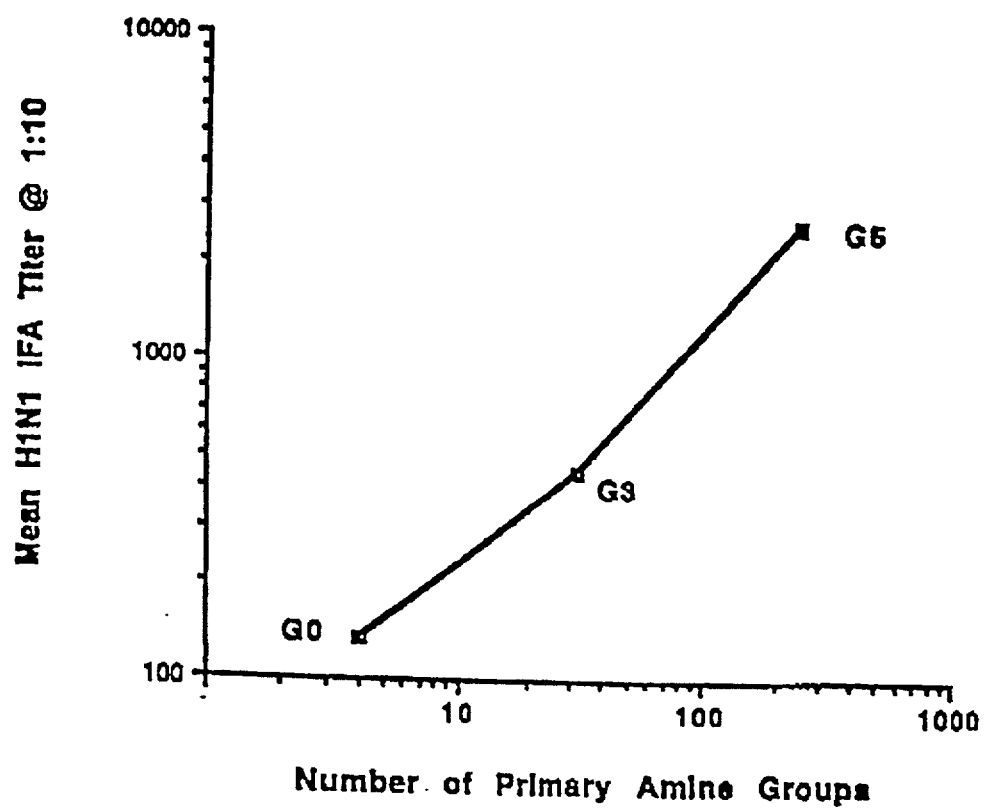

EXAMPLE II comparison of the adjuvanticity of three generations of dendrimers, G0, G3 and G6, prepared and administered as described in Example I above, in dilutions of 1:10 and 1:100, shows a correlation between the number of primary amine groups and the resulting mean IFA titer in mice. This data is summarized in Table 4, and illustrated graphically in FIG. 2. As can be seen from Table 4, an adjuvant effect is not produced with G0 dendrimers, while an effect is visible, but low, when G3 dendrimers are used. Dendrimers of Generation 6 are clearly effective adjuvants. As can be seen from FIG. 2, adjuvant effect correlates, in a substantially linear fashion, with the number of primary amine groups in each generation.

TABLE 4

Summary of Dendrimer Structure-Influenza Primary Immunization IFA Data in Mice

| Vaccine | Dendrimer Category | Molecular Weight | Number of Primary Amine Groups | Mean H1N1 IFA at 1:10 | Mean H1N1 IFA at 1:100 |
|---|---|---|---|---|---|
| G-0/TFlu PM | 0 | 517 | 4 | 134 | 15 |
| TFlu PM alone | NA | NA | NA | 47 | 17 |
| G-3/TFlu PM | 3 | 6909 | 32 | *448 | *154 |
| TFlu PM alone | NA | NA | NA | 47 | 17 |
| G-6/TFlu PM | 6 | 58048 | 256 | *2586 | *109 |
| TFlu PM alone | NA | NA | NA | 36 | 0.5 |

NA—Not Applicable
* = Adjuvant Effect

The foregoing example and description is merely illustrative of the invention. The invention is defined by the following claims and those skilled in the art will recognize there scope and the scope of equivalents thereof.

What is claimed is:

1. A vaccine for Influenza comprising an effective amount of a composition formed of an Influenza antigen and a starburst dendrimer in a physiologically compatible carrier; the amount of said Influenza antigen in said composition being substantially reduced from the amount necessary to yield a comparable antigenic response if given without said dendrimer.

2. The vaccine of claim 1 wherein said dendrimer comprises a poly(amidoamine) dendrimer.

3. The vaccine of claim 2 wherein said dendrimer is selected from the group consisting of Generation 3-Generation 10 dendrimers.

4. The vaccine of claim 3 wherein said dendrimer is selected from the group consisting of Generation 5-Generation 8 dendrimers.

5. The vaccine of claim 4 wherein said dendrimer is a Generation 6 dendrimer.

6. The vaccine of claim 1 wherein said Influenza antigen comprises multiple Influenza virus antigens.

7. The vaccine of claim 6 wherein said multiple antigens comprise trivalent split virus Influenza antigens.

8. The vaccine of claim 1 wherein said physiologically compatible carrier is selected from the group consisting of distilled water, phosphate buffered saline, normal saline, and mixtures thereof.

9. A method of preparing a vaccine for protection against Influenza which requires a lower level of antigen than conventional Influenza vaccines, the method comprising the steps of mixing an Influenza antigen with a starburst dendrimer, and diluting the mixture with a physiologically compatible carrier until said vaccine is prepared.

10. The method of claim 9 wherein said dendrimer comprises a poly(amidoamine) dendrimer.

11. The method of claim 10 wherein said dendrimer is selected from the group consisting of Generation 3-Generation 10 dendrimers.

12. The method of claim 11 wherein said dendrimer is selected from the group consisting of Generation 3-Generation 8 dendrimers.

13. The vaccine of claim 12 wherein said dendrimer is a Generation 6 dendrimer.

14. The method of claim 9 wherein said Influenza antigen comprises multiple Influenza virus antigens.

15. The method of claim 14 wherein said multiple antigens comprise trivalent split virus Influenza antigens.

16. The method of claim 9 wherein said physiologically acceptable carrier is selected from the group consisting of distilled water, phosphate buffered saline, normal saline, and mixtures thereof.

* * * * *